United States Patent [19]

Nakajima et al.

[11] 4,263,286

[45] Apr. 21, 1981

[54] THERAPEUTIC AGENT FOR CONSCIOUSNESS DISORDER AND PERCEPTION AND MOVEMENT DISORDER

[75] Inventors: Tadashi Nakajima, Takatsuki; Kyoji Rikimi, Osaka; Yasuji Soda, Kobe; Kenichi Kashima, Fujiidera; Akira Miyamoto, Nishinomiya; Yoshikazu Soejima, Osaka, all of Japan

[73] Assignee: Nippon Shoji Kaisha, Ltd., Osaka, Japan

[21] Appl. No.: 146,215

[22] Filed: May 5, 1980

Related U.S. Application Data

[62] Division of Ser. No. 16,340, Feb. 28, 1979, abandoned.

[30] Foreign Application Priority Data

Feb. 28, 1978 [JP] Japan .................................. 53/22385

[51] Int. Cl.$^3$ ........................ A23J 7/00; A61K 31/685
[52] U.S. Cl. ..................................... 424/199; 260/403
[58] Field of Search .......................... 424/199; 260/403

[56] References Cited

U.S. PATENT DOCUMENTS 3,772,360  11/1973  Pfeiffer et al. ....................... 260/403

*Primary Examiner*—Stanley J. Friedman
*Attorney, Agent, or Firm*—Stevens, Davis, Miller & Mosher

[57] ABSTRACT

A therapeutic agent for treating consciousness disorder and perception and movement which comprises as an essential active ingredient a phosphatidic acid derivative selected from a phosphatidylcholine, a phosphatidic acid and a phosphatidylethanolamine in admixture with a conventional carrier. Said agent is administered to the patient suffered from consciousness disorder and perception and movement disorder, particularly the post-traumatic syndrome of the head injury and the sequelae of apoplexy or whiplash injury in oral or parenteral route, preferably in an intravenous route.

12 Claims, 20 Drawing Figures

THERAPEUTIC AGENT FOR CONSCIOUSNESS DISORDER AND PERCEPTION AND MOVEMENT DISORDER

This is a division of application Ser. No. 16,340, filed Feb. 28, 1979, now abandoned.

The present invention relates to a therapeutic agent useful for treating consciousness disorder and perception and movement disorder. More particularly, it relates to a therapeutic agent comprising an essential active ingredient a phosphatidic acid derivative selected from phosphatidylcholines, phosphatidic acids and phosphatidylethanolamines.

It is well known that phosphatidylcholines, i.e. lecithins, have excellent biological activities and are useful as a medicine, and further that polyenephosphatidylcholine, which is a highly purified lecithin obtained from soy bean and composed mainly of 1,2-dilinoleoylphosphatidylcholine, exhibits excellent effect on hepatic disorders and hence are useful for treating various hepatic diseases such as hepatitis and fatty liver.

As the results of the present inventors' extensive studies on the pharmacological activities of lecithins and their analogues, it has newly been found that some phosphatidic acid derivatives have excellent therapeutic effects on consciousness disorder and perception and movement disorder.

Recently, with increase of various accidents (e.g. automobile accident) and apoplexy which is main cause of death in old aged people due to increase of old aged population, a lot of patients having consciousness disorder and perception and movement disorder appear, and hence, it becomes one of the most important problems to find a therapeutic agent useful for treating these diseases. Some medicines, such as Citicoline (i.e. cytidine diphosphate choline), Meclofenoxate hydrochloride (i.e. (4-chlorophenoxy)acetic acid 2-(dimethylamino)ethyl ester hydrochloride) or Pyrithioxin (i.e. 3,3'-(dithiodimethylene)-bis[5-hydroxy-6-methyl-4-pyridinemethanol)], have already been developed and used for the treatment of patients with consciousness disorder and perception and movement disorder.

It has now been found that some phosphatidic acid derivatives arouse consciousness and intensify motility of the pyramidal system and are effective on consciousness disorder and perception and movement disorder, and hence, these compounds are useful as a therapeutic agent for treating consciousness disorder and perception and movement disorder and have value as a medicine similar to or greater than the above known medicines, in view of the extremely low toxicity thereof.

An object of the present invention is to provide a new therapeutic agent useful for treating consciousness disorder and perception and movement disorder. Another object of the invention is to provide a method for treating consciousness disorder and perception and movement disorder by administering a new therapeutic agent comprising as an essential active ingredient a phosphatidic acid derivative. These and other objects and advantages of the present invention will be apparent from the following description.

The therapeutic agent for treating consciousness disorder and perception and movement disorder of the present invention comprises as an essential active ingredient a phosphatidic acid derivative selected from the group consisting of a phosphatidylcholine of the formula:

wherein $R_1$ and $R_2$ are the same or different and are each hydrogen or a residue of a fatty acid, provided that at least one of $R_1$ and $R_2$ is a residue of a fatty acid, a phosphatidic acid of the formula:

wherein $R_3$ and $R_4$ are the same or different and are each hydrogen or a residue of a fatty acid, provided that at least one of $R_3$ and $R_4$ is a residue of a fatty acid, or a salt thereof (e.g. a salt of an alkali metal such as sodium potassium, an alkaline earth metal such as magnesium, calcium, ammonium, or an organic base such as ethanolamine, trimethylol aminomethane, or choline), and a phosphatidylethanolamine of the formula:

wherein $R_5$ and $R_6$ are the same or different and are each hydrogen or a residue of a fatty acid, provided that at least one of $R_5$ and $R_6$ is a residue of a fatty acid.

In the above formula, the residue of a fatty acid for $R_1$ to $R_6$ includes a residue of a saturated fatty acid having 6 to 22 carbon atoms, such as hexanoic acid, capric acid, lauric acid, myristic acid, palmitic acid, stearic acid arachic acid and behenic acid, and a residue of an unsaturated fatty acid having 14 to 20 carbon atoms, such as myristoleic acid, palmitoleic acid, oleic acid, linoleic acid, linolenic acid and arachidonic acid. Preferably, at least one of $R_1$ and $R_2$, of $R_3$ and $R_4$, or of $R_5$ and $R_6$ is a residue of an unsaturated fatty acid, particularly a highly unsaturated fatty acid such as linoleic acid, linolenic acid and arachidonic acid. Besides, in the above formula [I], [II] and [III], when one of $R_1$ and $R_2$, of $R_3$ and $R_4$, or of $R_5$ and $R_6$ is hydrogen, these compounds are called as a lyso type compound, that is, lysophosphatidylcholines, lysophosphatidic acids, and lysophosphatidylethanolamines, respectively.

Suitable examples of the phosphatidic acid derivatives are 1,2-dihexanoylphosphatidylcholine, 1,2-dilinoleoylphosphatidylcholine, 1-linoleoyl-2-linolenoylphosphatidylcholine, 1-palmitoyl-2-linoleoylphosphatidylcholine, 1-linoleoyl-2-palmitoylphosphatidylcholine, 1-linoleoyl-2-arachidonylphosphatidylcholine, 1-linolenoyl-2-linoleoylphosphatidylcholine, 1,2-dilinolenoylphosphatidylcholine, 1-linolenoyl-2-arachidonylphosphatidylcholine, 1-arachidonyl-2-linoleoylphosphatidylcholine, 1-arachidonyl-2-linolenoylphosphatidylcholine, 1,2-arachidonylphosphatidylcholine, 1-palmitoyl-2-linoleoylphosphatidic acid disodium salt, 1-linoleoyl-2-palmitoylphosphatidic acid disodium salt, dilinoleoylphosphatidic acid or disodium salt thereof, diarachidonylphosphatidic acid disodium salt, or the like.

These phosphatidic acid derivatives include both natural products and synthetic or semisynthetic products, for instance, lecithins obtained from various plants such as soy bean, corn, rape seed or peanut, and lecithins obtained from various animal organs such as bovine brain, or eggs. These natural lecithins contain a residue of highly unsaturated fatty acids, and highly purified products are preferred. Suitable examples of such natural or semisynthetic products are soy bean phosphatidylcholine, soy bean phosphatidic acid disodium salt, soy bean phosphatidylethanolamine, soy bean lysophosphatidylcholine, soy bean lysophosphatidic acid disodium salt, soy bean lysophosphatidylethanolamine, yolk phosphatidylcholine, and yolk phosphatidic acid disodium salt. Processes for the synthesis of the phosphatidic acid derivatives include various known processes, but preferred process is disclosed in Japanese Patent Publication (unexamined) No. 91213/1976 and U.S. Pat. No. 4,130,571, which can give highly pured products. Other literatures disclosing processes for the preparation of phosphatidic acid derivatives are Biochem. J., Vol. 69, page 458 (1958), ibid., Vol. 102, page 205 (1967), and ibid., Vol. 102, page 221 (1967).

The phosphatidic acid derivatives of the present invention can administered to the patients in oral or parenteral route, such as intramuscular injection, intravenous drip injection or intravenous injection, among which the intravenous drip injection and intravenous injection are preferred. The injections are usually used in the form of an aqueous solution, in which there may usually be incorporated various conventional additives, such as solubilizers (e.g. bile acids selected from deoxycholic acid, apocholic acid, chenodeoxycholic acid, taurocholic acid, cholic acid, or the like), agents for making isotonic (e.g. glucose, sodium chloride, potassium chloride, calcium chloride, or the like), stabilizers (e.g. ethanol, α-tocopherol, nicotinamide, or the like), preservatives (e.g. benzyl alcohol, phenol, or the like), and pH adjustors (e.g. sodium hydroxide, potassium hydroxide, calcium hydroxide, or the like). For oral administration, the active compound can be used in the form of conventional preparations, such as tablets, capsules, powders, or liquids (e.g. suspensions, solutions, emulsions or syrups), in admixture with conventional pharmaceutical organic or inorganic carrier materials suitable for enteral application. In order to prepare an aqueous preparation, the active compound may be dissolved, suspended or emulsified into an aqueous medium mechanically, for instance, by means of ultrasonic.

The preparation for oral administeration of the present invention contains 5 to 5,000 mg, preferably 10 to 2,000 mg, of the phosphatidic acid derivative in a dose unit, which may usually be administered one to three times per day in adult. The preparation for injection contains 0.5 to 500 mg. preferably 1 to 100 mg, of the phosphatidic acid derivative in a dose unit. The preparation for injection may usually be administered one time per day in adult, but may be administered two or three times per day. Thus, the active compound may be administered in a dose of 10 mg to 15 g, preferably 50 mg to 10 g, for oral route, or in a dose of 1 to 1,500 mg, preferably 10 to 500 mg, for parenteral route, in adult. In children a smaller amount may be used, but in view of the low toxicity, the same amount as in adult may also be administered in children.

The pharmacological activities of the phosphatidic acid derivatives of the present invention, which have experimentally been confirmed, are illustrated below with reference to the accompanying drawings.

The therapeutic activities of drugs for consciousness disorder and perception and movement disorder are usually evaluated from the results of experiments on the arousal reaction and the evoked muscular discharges in the fore- and hind-limbs by stimulation of the brain stem reticular formation and on the evoked muscular discharges in the fore- and hind-limbs by stimulation of the cerebral cortex and the hippocampus [cf. Seiichi Fujimoto, J. Kansai Med. Sch., Vol. 21, NC. 3, pages 26–52 (Sept., 1969); Yasuhara et al, Kiso-to-Rinsho, Vol. 9, No. 2, pages 7–14 (Jan., 1975), and ibid, Vol. 9, No. 11, pages 151–158 (Oct. 1975)]. The activities of the phosphatidic acid derivatives of the present invention have been evaluated likewise as shown below.

The following experiments were done by using rabbits on the arousal reaction and evoked muscular discharges by stimulation of the brain stem reticular formation and also by stimulation of the cerebral cortex and the hippocampus. From the results on the arousal reaction and evoked muscular discharges by stimulation of the brain stem reticular formation, the effects of the test compounds on the function of brain to the consciousness and movement are evaluated. That is, when the brain stem reticular formation is stimulated and the EEG (electroencephalogram) of the cerebral cortex and the hippocampus are recorded, the arousal reaction appears. In this case, when a drug having an action of arousing consciousness is administered, an arousal reaction is observed on the EEG at the cerebral cortex and the hippocampus even if the electrical stimulus is reduced, and hence, the effect of the test compound on the arousing consciousness is evaluated from the relation between the amount of the test compound and the degree of reduction of electrical stimulus which is necessary for the occurrence of the arousal reaction. The effect of the test compound on the movement is also examined by simultaneously recording the evoked muscular discharges in the fore- and hind-limbs.

Moveover, from the results on the evoked muscular discharges by stimulation of the cerebral cortex, there can be evaluated the effects of the test compound on the functions of brain to the movement, particularly on the function of the pyramidal system which participates in the voluntary movement. That is, when the cerebral cortex is stimulated, a tonic type muscular discharge more often appears in the forelimb than in the hindlimb of rabbit, and these muscular discharges are increased in amplitude and are prolonged by administration of a drug which has an action of facilitating the system which participates the voluntary movement. Accordingly, from the relation between the amount of the test compound and the degree of facilitation of the muscular discharges, the effects of the test compound on the voluntary movement can be evaluated.

The experiments on the muscular discharges by stimulation of the hippocampus are carried out for the purpose of examination of the function of the extrapyramidal system which participates in the involuntary movement. When an electrical stimulus is applied to the hippocampus, mainly a phasic type muscular discharge appears in the fore- and hind-limbs of rabbit, and hence, by observing the variation of the amplitude and prolongation of the muscular discharges, the effects of the test compound on the facilitation of involuntary movement can also be evaluated.

Moreover, in order to test the effects of the test compounds in a symptom similar to a clinical state (e.g. apoplexy or brain operation), particularly to test the effects on the motility of the pyramidal system, the internal capsule in rabbits is destroyed and then an electrical stimulus is given to the cerebral cortex, and the muscular discharges in the fore- and hind-limbs were measured.

EXPERIMENT 1

Experiment of the arousal reaction and the evoked muscular discharges in normal rabbits Method: In the same manner as described in Yasuhara et al, Current Therapeutic Research, Vol. 16, No. 4, pages 346-374 (April, 1974), particularly in page 347 thereof, normal rabbits (one group: 5 rabbits) were given by an electrical stimulus without anesthesia, and a test compound (in the form of a composition as disclosed in Example 1 hereinafter: highly purified soy bean lecithin, 0.3, 0.5, 1, 3 and 5 mg/kg as converted to the lecithin) was intravenously injected, and the effects were observed.

Figure 1:
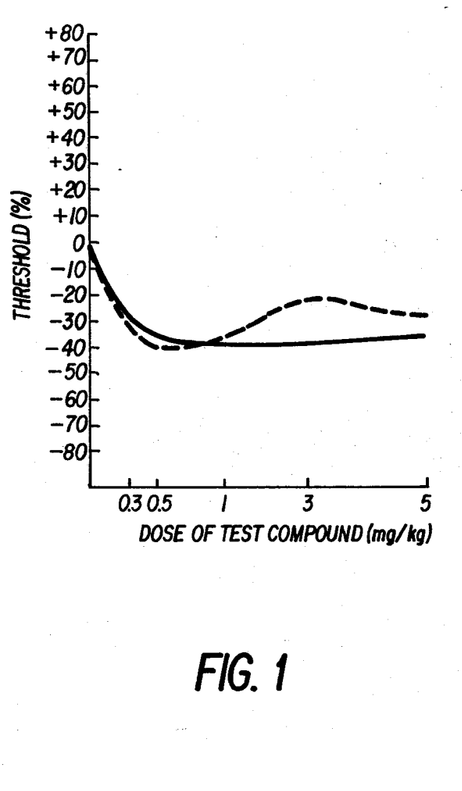
Figure 2:
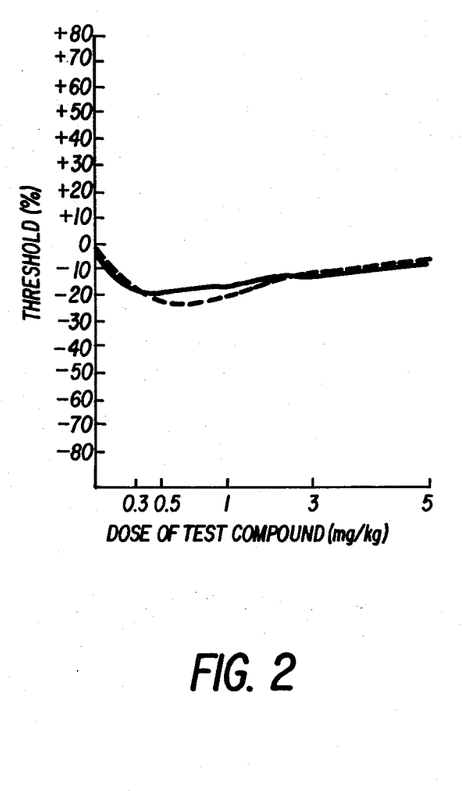

Results (a) In case of stimulation of the brain stem reticular formation:

When an electrical stimulus of 100 Hz was applied to the brain stem reticular formation, before administering the test compound, the threshold of arousal reaction in one rabbit was 0.8 V in the cerebral cortex and 0.7 V in the hippocampus and the thresholds of evoked muscular discharges in the fore- and hind-limbs were 0.8 V, but after administering 5 mg/kg of the lecithin, the thresholds of arousal reaction decreased to 0.4 V both in the cerebral cortex and the hippocampus and the thresholds of the evoked muscular discharges in the fore- and hind-limbs decreased to 0.6 V. The change of the thresholds before and after the administration of the test compound was shown in percentage. The accompanying FIGS. 1 and 2 show the change in average. In these figures, the abscissa axis means the amount of the test compound, the ordinate axis means the percentage of the change of thresholds, and the upper part is an increase of the thresholds (+), the lower part is a decrease of the thresholds (-), and the point 0 is the control (i.e. the value before administration of the test compound).

FIG. 1 shows the change of the thresholds of the arousal reaction, wherein the solid line means the data of the cerebral cortex and the dotted line means the data of the hippocampus. As is clear from the data, the thresholds of the arousal reaction in the cerebral cortex and the hippocampus were decreased more than 35% in average by the administration of the test compound.

FIG. 2 shows the change of the thresholds of the evoked muscular discharges, wherein the solid line means the data in the forelimb and the dotted line means the data in the hindlimb. As is clear from the data, the thresholds of the evoked muscular discharges were decreased about 20% by the administration of the test compound.

By the way, while the thresholds in these FIGS. 1 and 2 tend to increase with increase of the amount of the test compound, it may spontaneously increase with the lapse of time, because in case of injection of a physiological saline solution (reference) they also increase.

(b) In case of stimulation of the cerebral cortex and hippocampus:

After experiments by the stimulation of the brain stem reticular formation as above, the effects of the test compound on the muscular discharges evoked by stimulation of the cerebral cortex and the hippocampus were also tested. As the results, when the cerebral cortex was stimulated, after intravenous injection of 0.3 mg/kg to 5 mg/kg of the test compound, the muscular discharges in the hindlimb was almost not changed, but the muscular discharges in the forelimb was clearly facilitated. Thus, the compound of the present invention showed a facilitatory effect on the motility of the pyramidal system.

On the other hand, in case of stimulation of the hippocampus, different action was observed. That is, when the compound of the present invention was intravenously injected in a dose of 3 mg/kg to 5 mg/kg, the muscular discharges of extensor muscle and flexor muscle in both of the fore- and hind-limbs was inhibited. Thus, the stimulation of the hippocampus showed inhibitory action in the contrary to the stimulation of the cerebral cortex, and hence, the compound of the present invention showed an inhibitory effect on the motility of the extrapyramidal system.

From the above experimental results, it is clear that the compound of the present invention has a facilitatory effect on consciousness and is effective particularly on the motility of the pyramidal system, i.e. on the voluntary movement.

EXPERIMENT II

The arousal reaction and the evoked muscular discharges in normal rabbits were experimented in the same manner as described in Experiment I except that a composition as disclosed in Example 2 hereinafter (synthetic lecithin) was used as the test compound.

Figure 3:
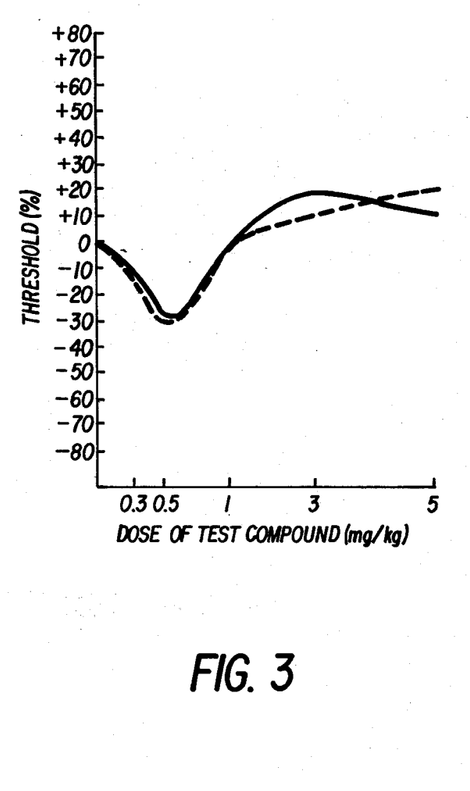
Figure 4:
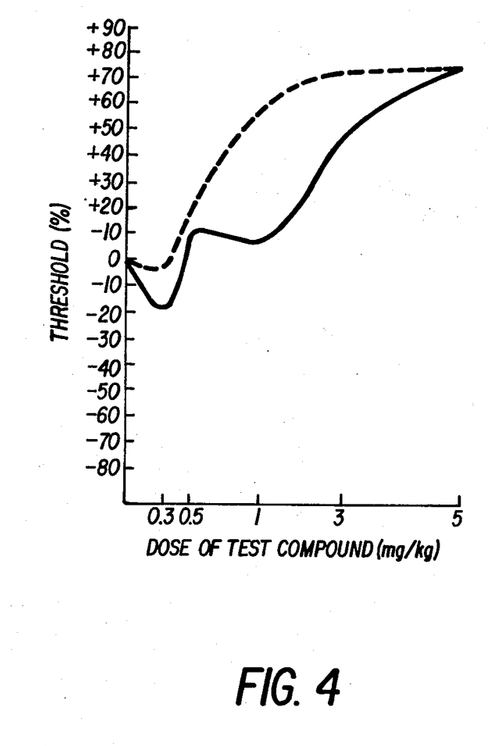
Figure 5:
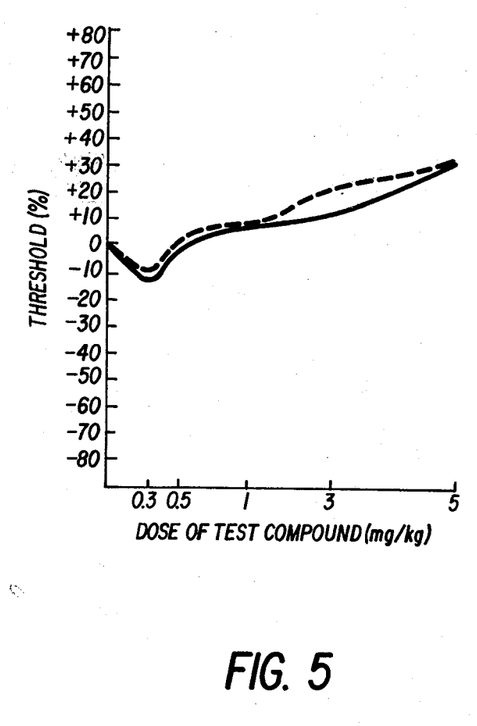
Figure 6:
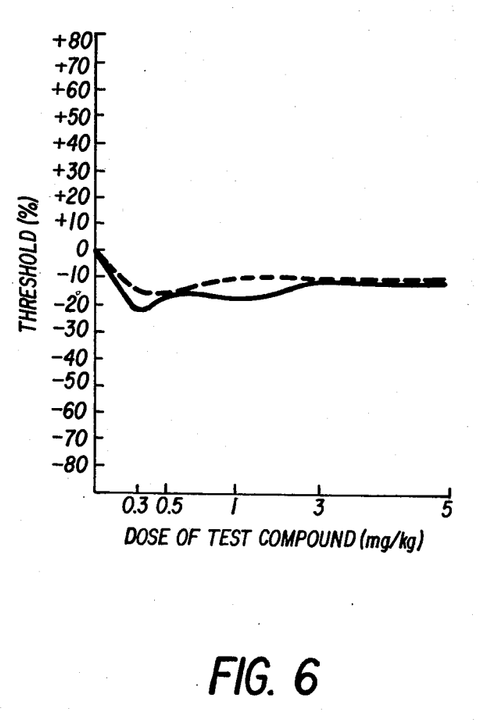
Figure 7:
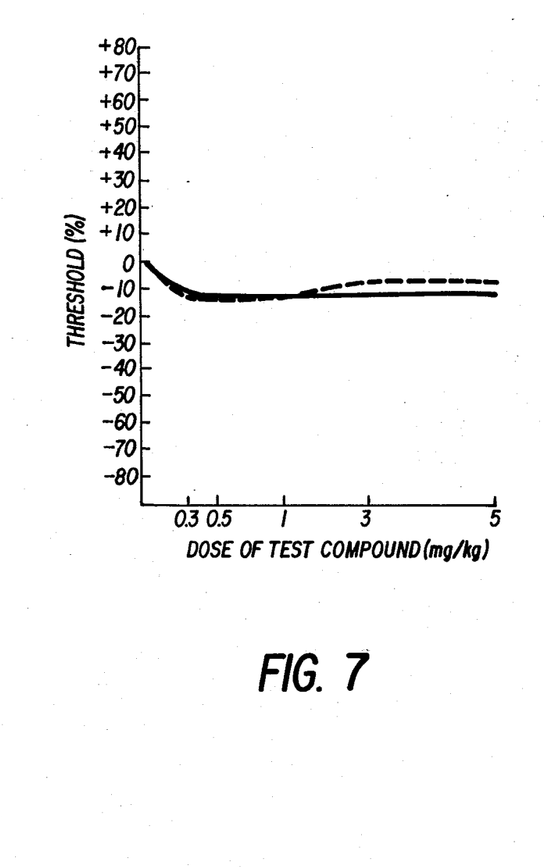
Figures 8, 9:
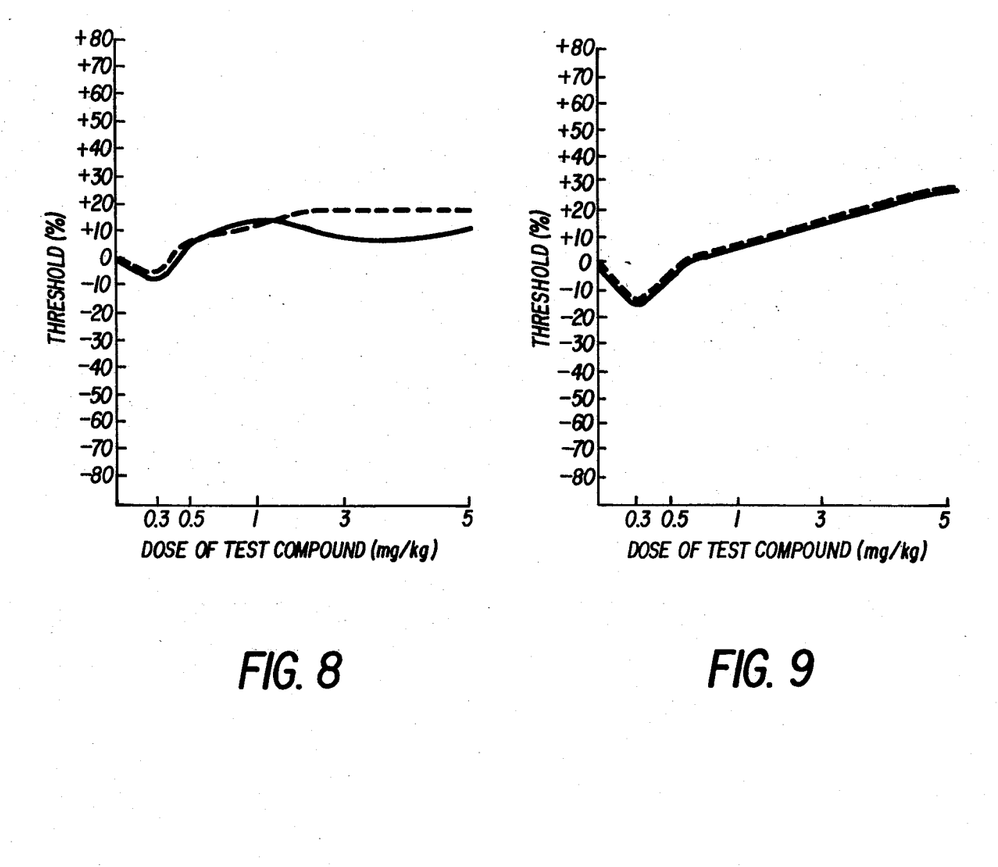
Figure 10:
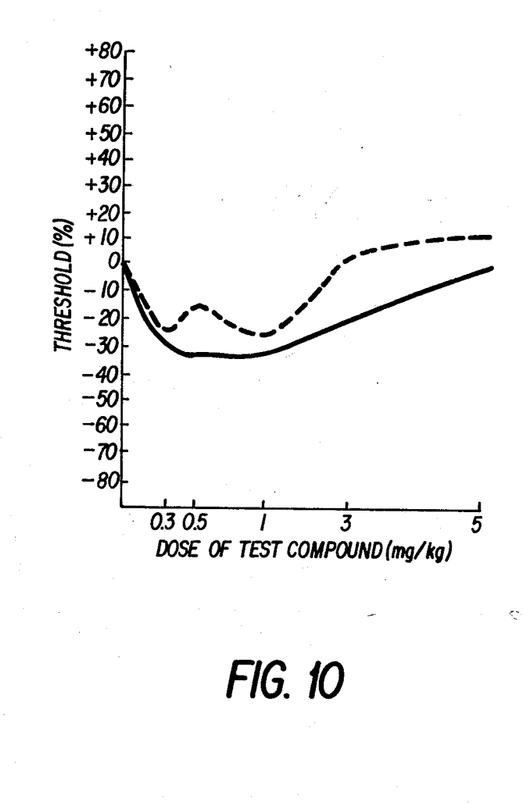
Figure 11:
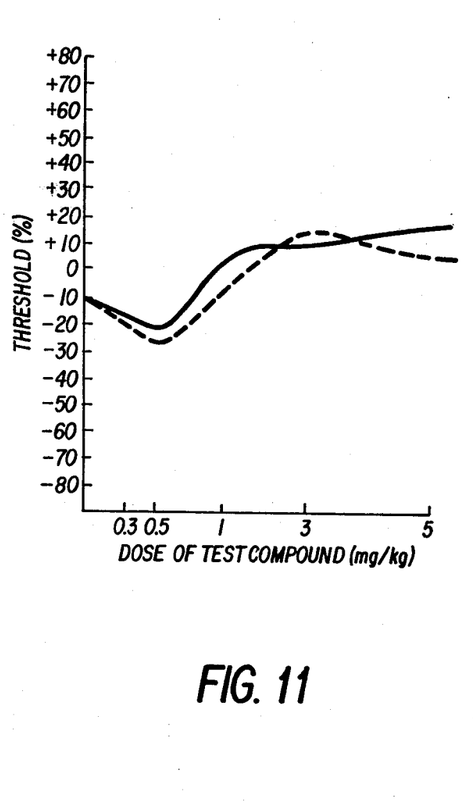
Figure 12:
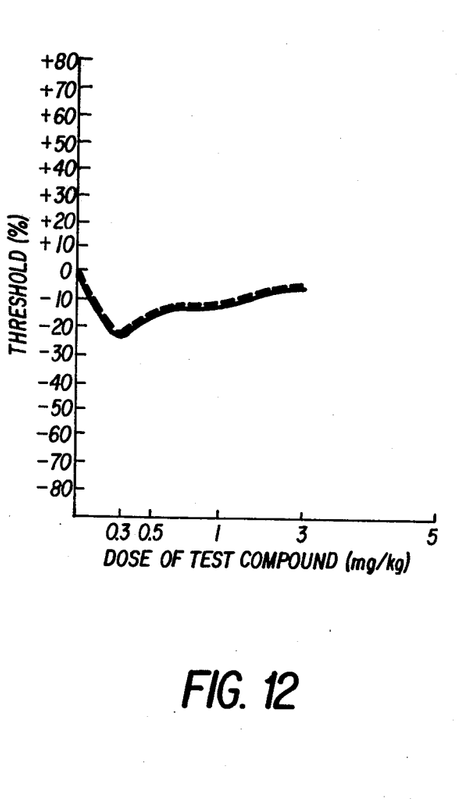
Figure 13:
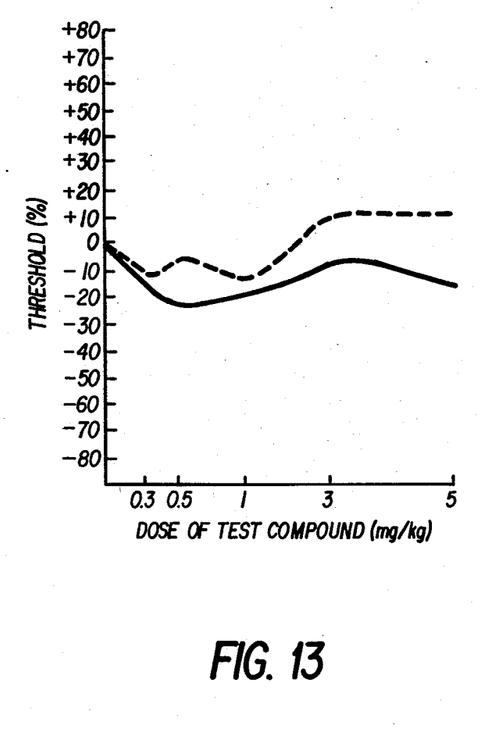
Figure 14:
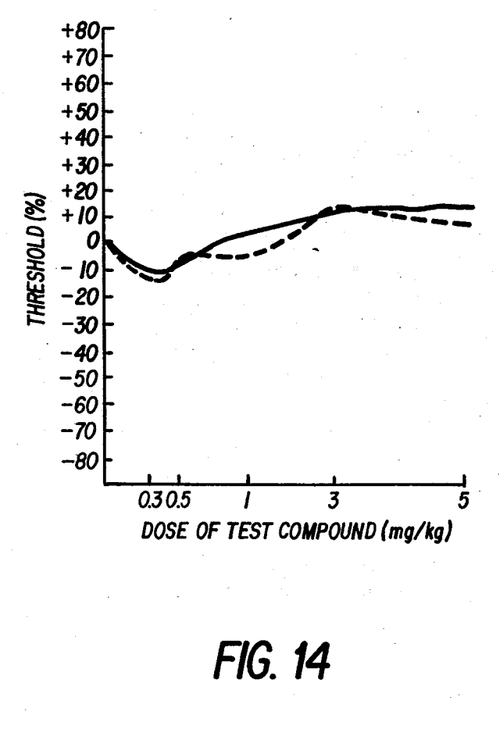

The experimental results in case of stimulation of the brain stem reticular formation are shown in the accompanying FIGS. 3 and 4. FIG. 3 shows the change of the thresholds of the arousal reaction, and FIG. 4 shows the change of the thresholds of the evoked muscular discharges. The same explanations as used in FIGS. 1 and 2 are applied to these figures likewise.

As is clear from these experimental results, when a synthetic lecithin was administered in a dose of 0.3 mg/kg to 1 mg/kg, the thresholds of the arousal reaction and the evoked muscular discharges in the forelimb decreased about 30% in average and about 20% in average, respectively. Accordingly, the synthetic lecithin showed the same effects as those of soy bean lecithin on the consciousness and movement.

EXPERIMENT III

The arousal reaction in case of stimulation of the brain stem reticular formation in normal rabbits was experimented in the same manner as described in Experiment I except that soy bean phosphatidic acid disodium salt, soy bean lysophosphatidylcholine, soy bean lysophosphatidic acid disodium salt, soy bean lysophosphatidylethanolamine, yolk phosphatidic acid disodium salt, dihexanoylphosphatidylcholine, diarachidonylphosphatidylcholine, diarachidonylphosphatidic acid disodium salt, dilinoleoylphosphatidic acid disodium salt, and 1-linoleoyl-2-palmitoylphosphatidic acid disodium salt were used as the test compounds. The experimental results are shown in FIGS. 5, 6, 7, 8, 9, 10, 11, 12, 13 and 14, respectively.

EXPERIMENT IV

Experiment of the arousal reaction and the evoked muscular discharges in rabbits whose internal capsule was destroyed:

Method: An electrode for destroying the internal capsule was inserted into the internal capsule of rabbits and an electric current passed to the electrode and thereby the internal capsule was destroyed. To such treated rabbits was administered the test compound in order to examine the effects thereof on the threshold of muscular discharges in the fore- and hind-limbs by stimulation of the cerebral cortex. The test compound (in the form of composition as described in Example 1 hereinafter) was intravenously injected in a dose of 0.5 mg/kg or 1.0 mg/kg (converted to lecithin) every day. The thresholds were measured before destruction of internal capsule, immediately after destruction, and one to four weeks after destruction.

Results

As reference experiments, without administering the test compound, the change of the thresholds of the evoked muscular discharges in the fore- and hind-limbs by stimulation of the cerebral cortex was observed. The results are shown in Table 1. In the table, the thresholds are shown by a number of voltage (V), and the percentage change (%) means a percentage of the change of the thresholds after destruction of internal capsule to the thresholds before destruction, and the abbreviations mean respectively as follows:

FC: EEG of cerebral cortex
FEMG: Evoked muscular discharge of forelimb
HEMG: Evoked muscular discharge of hindlimb

TABLE 1

| Number of test animals | Before destruction of internal capsule | After destruction of internal capsule ||||||||
|---|---|---|---|---|---|---|---|---|---|
| | | Immediately after destruction | % | One week after destruction | % | Two weeks after destruction | % | Three weeks after destruction | % | Four weeks after destruction | % |
| FC | 3 | 3 | 0 | 5 | 67 | 6 | 100 | 4 | 33 | 4 | 33 |
| 1 FEMG | 3 | 8 | 167 | 5 | 67 | 6 | 100 | 4 | 33 | 4 | 33 |
| HEMG | 3 | 8 | 167 | 5 | 67 | 6 | 100 | 4 | 33 | 7 | 133 |
| FC | 2 | 4 | 100 | 3 | 50 | 3 | 50 | 4 | 100 | 4 | 100 |
| 2 FEMG | 2 | 5 | 150 | 3 | 50 | 3 | 50 | 4 | 100 | 4 | 100 |
| HEMG | 3 | 6 | 100 | 6 | 100 | 4 | 33 | 8 | 167 | 8 | 167 |
| FC | 2 | 2.4 | 20 | 2.6 | 30 | 2.4 | 20 | 3 | 50 | 3 | 50 |
| 3 FEMG | 2.4 | 3 | 25 | 3 | 25 | 3 | 25 | 3 | 25 | 3 | 25 |
| HEMG | 3 | 4 | 33 | 4 | 33 | 4 | 33 | 4 | 33 | 3 | 0 |
| FC | 1.6 | 3 | 88 | 6 | 275 | 4 | 150 | 4 | 150 | 4 | 150 |
| 4 FEMG | 2.4 | 5 | 108 | 6 | 150 | 6 | 150 | 6 | 150 | 5 | 108 |
| HEMG | 2.8 | 5 | 79 | 6 | 114 | 6 | 114 | 6 | 114 | 6 | 114 |
| FC | 2 | 2 | 0 | 8 | 300 | 10 | 400 | 8 | 300 | 10 | 400 |
| 5 FEMG | 4 | 10 | 150 | 10 | 150 | 15 | 275 | 10 | 150 | 20 | 400 |
| HEMG | 6 | 10 | 67 | 10 | 67 | 15 | 150 | 12 | 100 | 20 | 233 |
| Average FC | — | — | 42 | — | 144 | — | 144 | — | 127 | — | 147 |
| FEMG | — | — | 120 | — | 88 | — | 120 | — | 92 | — | 133 |
| HEMG | — | — | 89 | — | 76 | — | 86 | — | 89 | — | 129 |

As is clear from Table 1, immediately after destruction of internal capsule, the percentage change of the thresholds by stimulation of the cerebral cortex increased to 120% in average in the forelimb and to 89% in average in the hindlimb, and four weeks after destruction, the percentage change increased to 133% in average in the forelimb and to 129% in average in the hindlimb.

Following the above reference experiment, the test compound was intravenously injected in a dose of 0.5 mg/kg or 1.0 mg/kg every day, and the thresholds of the evoked muscular discharges by stimulation of the cerebral cortex were measured. The results are shown in Tables 2 and 3.

TABLE 2

| | (Dose of test compound: 0.5 mg/kg) ||||||||||
|---|---|---|---|---|---|---|---|---|---|---|
| Number of test animals | Before destruction of internal capsule | After destruction of internal capusle ||||||||
| | | Immediately after destruction | % | One week after destruction | % | Two weeks after destruction | % | Three weeks after destructon | % | Four weeks after destruction | % |
| FC | 3 | 5 | 67 | 3 | 0 | 4 | 33 | 4 | 33 | 4 | 33 |
| 1 FEMG | 7 | 12 | 71 | 5 | −29 | 7 | 0 | 7 | 0 | 6 | −14 |
| HEMG | 7 | 20 | 186 | 5 | −29 | 7 | 0 | 7 | 0 | 6 | −14 |
| FC | 2 | 5 | 150 | 2 | 0 | 2 | 0 | 2 | 0 | 2 | 0 |
| 2 FEMG | 5 | 8 | 60 | 5 | 0 | 5 | 0 | 8 | 60 | 5 | 0 |
| HEMG | 5 | 8 | 60 | 5 | 0 | 5 | 0 | 8 | 60 | 5 | 0 |
| FC | 2 | 6 | 200 | 3 | 50 | 2 | 0 | 2 | 0 | 2 | 0 |
| 3 FEMG | 6 | 8 | 33 | 6 | 0 | 8 | 33 | 6 | 0 | 6 | 0 |
| HEMG | 8 | 15 | 88 | 8 | 0 | 10 | 25 | 10 | 25 | 6 | −25 |
| FC | 2 | 2 | 0 | 2 | 0 | 2 | 0 | 2 | 0 | 2 | 0 |
| 4 FEMG | 4 | 20 | 400 | 8 | 100 | 6 | 50 | 5 | 25 | 3 | −25 |
| HEMG | 4 | 20 | 400 | 15 | 275 | 6 | 50 | 6 | 50 | 3 | −25 |
| FC | 1 | 2 | 100 | 2 | 100 | 2 | 100 | 2 | 100 | 1 | 0 |
| 5 HEMG | 3 | 5 | 67 | 4 | 33 | 4.4 | 47 | 4.4 | 47 | 1.6 | −47 |
| HEMG | 3 | 12 | 300 | 5 | 67 | 4.4 | 47 | 4.4 | 47 | 1.6 | −47 |
| Average FC | — | — | 103 | — | 30 | — | 27 | — | 27 | — | 7 |

TABLE 2-continued (Dose of test compound: 0.5 mg/kg)

| | Before destruction of internal capsule | After destruction of internal capsule | | | | | | | |
|---|---|---|---|---|---|---|---|---|---|
| Number of test animals | | Immediately after destruction % | | One week after destruction % | | Two weeks after destruction % | | Three weeks after destructon % | | Four weeks after destruction % |
| FEMG | — | — | 126 | — | 21 | — | 26 | — | 26 | — | −17 |
| HEMG | — | — | 207 | — | 63 | — | 24 | — | 36 | — | −22 |

TABLE 3

(Dose of test compound: 1.0 mg/kg)

| | Before destruction of internal capsule | After destruction of internal capsule | | | | | | | | |
|---|---|---|---|---|---|---|---|---|---|---|
| Number of test animals | | Immediately after destruction | % | One week after destruction | % | Two weeks after destruction | % | Three weeks after destruction | % | Four weeks after destruction | % |
| FC | 3 | 3 | 0 | 8 | 167 | 8 | 167 | — | — | 3 | 0 |
| 1 FEMG | 4 | 8 | 100 | 10 | 150 | 14 | 250 | — | — | 4 | 0 |
| HEMG | 4 | 20 | 400 | 12 | 200 | 15 | 275 | — | — | 4 | 0 |
| FC | 4 | 7 | 75 | 5 | 25 | 4 | 0 | 2 | −50 | 2 | −50 |
| 2 FEMG | 4 | 15 | 275 | 5 | 25 | 4 | 0 | 3 | −25 | 2 | −50 |
| HEMG | 4 | 20 | 400 | 5 | 25 | 4 | 0 | 4 | 0 | 2 | −50 |
| FC | 3 | 8 | 167 | 5 | 67 | 3 | 0 | 3 | 0 | 3 | 0 |
| 3 FEMG | 3 | 8 | 167 | 16 | 433 | 12 | 300 | 6 | 100 | 4 | 33 |
| HEMG | 6 | 10 | 67 | 16 | 167 | 12 | 100 | 6 | 0 | 4 | −33 |
| FC | 1 | 8 | 700 | 3 | 200 | 1 | 0 | 1 | 0 | 1 | 0 |
| 4 FEMG | 1 | 8 | 700 | 7 | 600 | 6 | 500 | 1 | 0 | 1 | 0 |
| HEMG | 4 | 8 | 100 | 8 | 100 | 5 | 25 | 4 | 0 | 2 | −50 |
| FC | 1 | 3 | 200 | 2 | 100 | 2 | 100 | 1.6 | 60 | 1.6 | 60 |
| 5 FEMG | 2 | 5 | 150 | 3 | 50 | 2.4 | 20 | 2 | 0 | 2 | 0 |
| HEMG | 2 | 5 | 150 | 3 | 50 | 2.4 | 20 | 2 | 0 | 2 | 0 |
| Average | | | | | | | | | | | |
| FC | 2.4 | — | 228 | — | 112 | — | 53 | — | 3 | — | 2 |
| FEMG | 2.8 | — | 278 | — | 252 | — | 214 | — | 19 | — | −3 |
| HEMG | 4 | — | 223 | — | 108 | — | 84 | — | 0 | — | −27 |

As is clear from the above results, when the test compound was intravenously injected in a dose of 0.5 mg/kg every day, immediately after destruction of internal capsule, the percentage change of the thresholds by stimulation of the cerebral cortex increased to 126% in average in the forelimb and to 207% in average in the hindlimb; one week after destruction, the percentage change decreased to 21% in average in the forelimb and to 63% in average in the hindlimb; two weeks after destruction, it became 26% in average in the forelimb and 24% in average in the hindlimb; and four weeks after destruction it decreased to −17% in average in the forelimb and −22% in average in the hindlimb.

When the test compound was administered in a dose of 1.0 mg/kg, immediately after destruction of internal capsule, the percentage change increased to 278% in average in the forelimb and to 223% in average in the hindlimb; one and two weeks after destruction, the percentage change was almost not found and those of the forelimb after one and two weeks were 252% and 214% in average, respectively; but three weeks after destruction, it became 19% in average in the forelimb and 0 in the hindlimb; and four weeks after destruction, it decreased to −3% in average in the forelimb and −27% in average in the hindlimb, which were lower than the values before destruction as like as the case of administration of the test compound in a dose of 0.5 mg/kg.

Thus, in the experiments using rabbits having destroyed internal capsule, when no test compound was administered, the thresholds of the evoked muscular discharges by stimulation of the cerebral cortex significantly increased, but when the test compound was administered, the thresholds significantly decreased. The effects of the test compound was stronger in case of administration of the test compound of 0.5 mg/kg than that in a dose of 1.0 mg/kg.

It has already been confirmed by experiments that Cytochrome C, Citicoline, Meclofenoxate hydrochloride and Pyrithioxin, which have already been used as therapeutic agents for the treatment of consciousness disorder and perception and movement disorder, have also decreasing effect of the thresholds of evoked muscular discharge in the fore- and hind-limbs by stimulation of the cerebral cortex in rabbits having destroyed internal capsule. Thus, it was now confirmed that the compound of the present invention had the same effect as that of these known therapeutic agents.

EXPERIMENT V

In order to test the effect of the active compound of the present invention on perception, an experiment was carried out on afferent evoked potential in response to stimulation of the sciatic nerve.

When the sciatic nerve is stimulated, the potential evoked in the cerebral cortex is recorded and summed up. These evoked electric potentials are firstly three small negative responses, subsequently a positive response and followed by two large negative responses, which are designated as $N_1$, $N_2$, $N_3$, P, $N_4$ and $N_5$, respectively.

In order to examine the effect of a compound of the present invention: dilinoleoylphosphatidic acid disodium salt on these components, $N_1$, $N_2$, $N_3$, P, $N_4$ and $N_5$, sciatic nerve was simulated once per 1 second and the data of 50 times of stimulus were recorded and summed up. The results are shown in the accompanying FIGS. 15, 16, 17, 18, 19 and 20 which correspond to the data of $N_1$, $N_2$, $N_3$, P, $N_4$ and $N_5$, respectively. In these figures, the ordinate axis means the change of the value of each component and the upper part is an increase of the value (+) and the lower part is a decrease of the value (−), and the point 0 is the control (i.e. the value before administration of the test compound), and the graph shows the average of the change, and the abscissa axis means the amount of the test compound.

Figure 15:
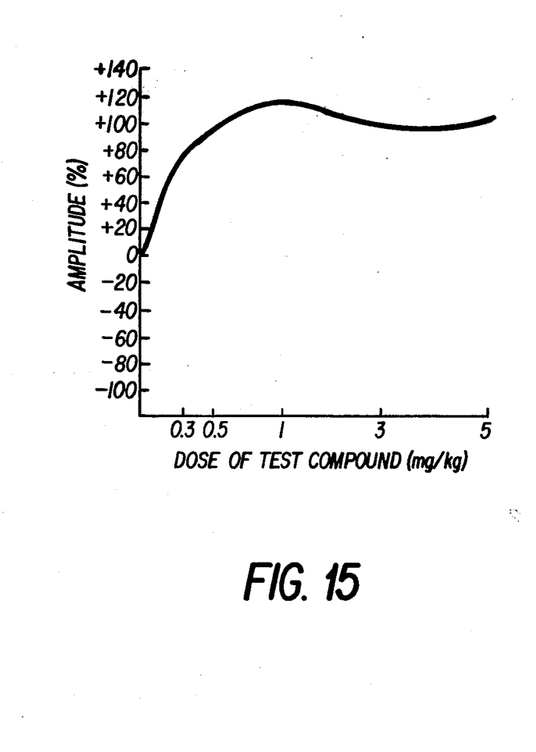
Figure 16:
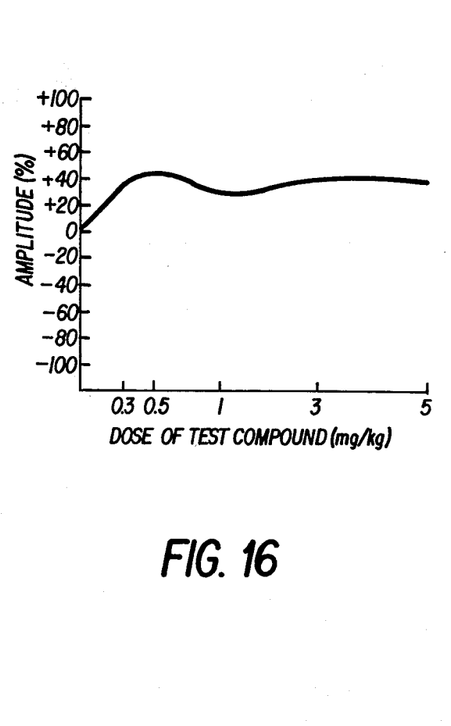
Figure 17:
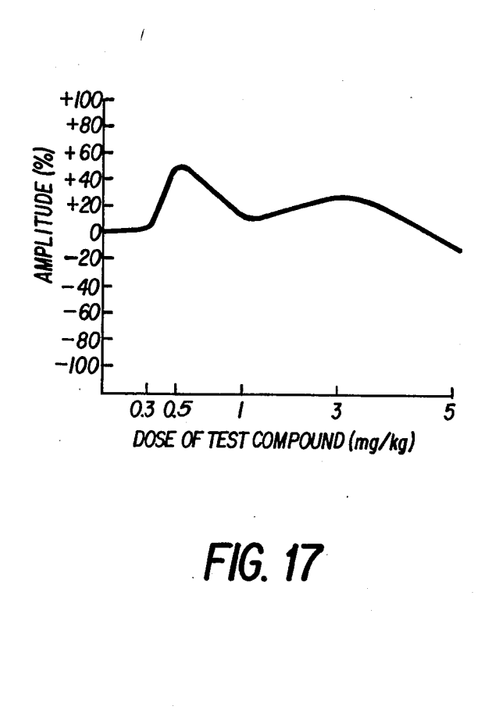
Figure 18:
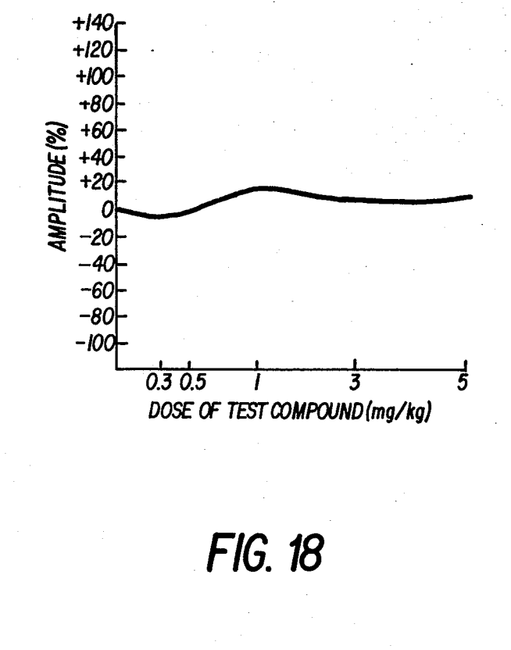
Figure 19:
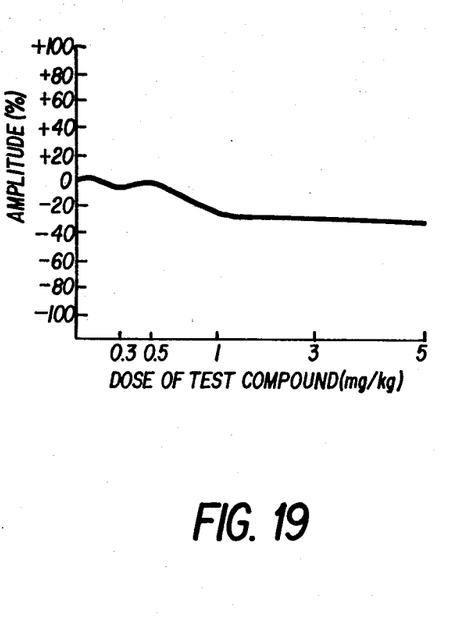
Figure 20:
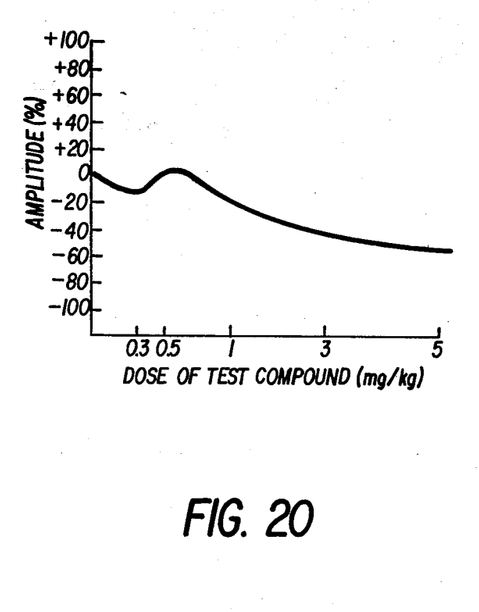

As is clear from the results, dilinoleoylphosphatidic acid disodium salt showed a facilatory effect on the components, $N_1$ and $N_2$, particularly on $N_1$, which have a close relation with the perception. Since the early components such as $N_1$ and $N_2$ appear mainly after ascending the afferent pathway from the peripheral to the cerebral cortex, it is clear from the test results that the compound of the present invention has a facilitatory effect on the afferent pathway.

TOXICITY

The compounds of the present invention are characteristic in remarkedly low toxicity.

For example, when polyenephosphatidylcholine (soy bean phosphatidylcholine) was administered to 4 week age ICR mice for 7 days in intravenous, intraperitoneal, subcutaneous and oral routes in a dose of 4,000 mg/kg, 10,000 mg/kg, 10,000 mg/kg, and 10,000 mg/kg, respectively, no mouse was died. Besides, when polyenephosphatidylcholine was administered to Spragne-Dowley rats for 7 days in intravenous, intraperitoneal, subcutaneous and oral routes in a dose of 2,000 mg/kg, 4,000 mg/kg, 4,000 mg/kg, and 6,000 mg/kg, respectively, no rat was died. Moreover, in all animals, no abnormal symptom was observed except that the voluntary movement was slightly inhibited in the groups administered in a large dose of the compound. There is no difference between male and female in both animals.

Acute toxicity of the composition as described in Example 1 hereinafter was tested by using Wistar male rats and rabbits, wherein 72 hours after administration of the compound, the rate of death was observed. In rats, the $LD_{50}$ in intraperitoneal administration was 18.3 ml/kg (converted into polyenephosphatidylcholine, 915.0 mg/kg), and the $LD_{50}$ in intravenous injection was 16.2 ml/kg (converted into polyenephosphatidylcholine, 810.0 mg/kg). In case of rabbits, the $LD_{50}$ in intravenous injection was 10.0 ml/kg (converted into polyenephosphatidylcholine, 500.0 mg/kg).

Besides, dilinoeoylphosphatidic acid disodium salt was administered to male mice weighing 25 g in a dose of 100 mg/kg in a tail intravenous route for a period of 30 seconds, and the animals were observed for 75 hours. As the result, no mouse was died.

CLINICAL TEST

Polyenephosphatidylcholine was administered to three human patients, a 64 age female patient suffered from brain infarction (thrombus) and having movement disorder of left arm and left limb and also consciousness disorder, a 56 age male patient suffered from brain infarction and having movement disorder of right arm and right limb, and a 39 age female patient suffered from the sequelae of apoplexy and having movement disorder of left arm and left limb. The compound was administered to these patients by an intravenous drip injection in a dose of 500 mg/10 ml. When these patients were treated for about two or three weeks, the disorders were improved.

The phosphatidic acid derivatives of the present invention are useful for the treatment of consciousness disorder and perception and movement disorder with high safety, particularly for the treatment of the post-traumatic syndrome of the head injury and the sequelae of apoplexy, and also whiplash injury.

The preparation of the composition of the present invention is illustrated by the following Examples.

EXAMPLE 1

| | | |
|---|---|---|
| Polyenephosphatidylcholine (highly purified soy bean lecithine) | | 50.0 mg |
| Deoxycholic acid | | 23.0 mg |
| Sodium chloride | | 3.5 mg |
| Sodium hydroxide | | 2.5 mg |
| Benzyl alcohol | | 9.0 mg |
| Distilled water | Total | 1.0 ml |

The above components are mixed to prepare 1 ml ampoule in a conventional manner.

EXAMPLE 2

| | | |
|---|---|---|
| 1,2-Dilinoleoylphosphatidylcholine (synthetic product) | | 50.0 mg |
| Deoxycholic acid | | 49.0 mg |
| Glucose | | 5.0 mg |
| Sodium hydroxide | | 3.0 mg |
| Benzyl alcohol | | 9.0 mg |
| Distilled water | Total | 1.0 ml |

The above components are mixed to prepare 1 ml ampoule in a conventional manner.

EXAMPLE 3

| | | |
|---|---|---|
| Soy bean phosphatidic acid disodium salt | | 25.0 mg |
| Deoxycholic acid sodium salt | | 39.0 mg |
| Glucose | | 50.0 mg |
| Benzyl alcohol | | 4.5 mg |
| Distilled water | Total | 1.0 ml |

The above components are mixed to prepare 1 ml ampoule in a conventional manner.

EXAMPLE 4

| | | |
|---|---|---|
| 1,2-Dilinoleoylphosphatidic acid disodium salt | | 25.0 mg |
| Deoxycholic acid sodium salt | | 35.0 mg |
| Glucose | | 50.0 mg |
| Benzyl alcohol | | 4.5 mg |
| Distilled water | Total | 1.0 ml |

The above components are mixed to prepare 1 ml ampoule in a conventional manner.

EXAMPLE 5

| | | |
|---|---|---|
| 1,2-Dilinoleoylphosphatidic acid disodium salt | | 25.0 mg |
| Glucose | | 50.0 mg |
| Benzyl alcohol | | 4.5 mg |
| Distilled water | Total | 1.0 ml |

The above components are mixed and the mixture is treated with an ultrasonic to prepare 1 ml ampoule.

EXAMPLE 6

| | | |
|---|---|---|
| Soy bean lysophosphatidylcholine | | 25.0 mg |
| Glucose | | 50.0 mg |
| Benzyl alcohol | | 4.5 mg |
| Distilled water | Total | 1.0 ml |

The above components are mixed and the mixture is treated with an ultrasonic to prepare 1 ml ampoule.

EXAMPLE 7

| | | |
|---|---|---|
| Soy bean phosphatidic acid disodium salt | | 25.0 mg |
| Glucose | | 50.0 mg |
| Benzyl alcohol | | 4.5 mg |
| Distilled water | Total | 1.0 ml |

The above components are mixed and the mixture is treated with an ultrasonic to prepare 1 ml ampoule.

EXAMPLE 8

| | | |
|---|---|---|
| 1,2-Dihexanoylphosphatidylcholine | | 25.0 mg |
| Glucose | | 50.0 mg |
| Benzyl alcohol | | 4.5 mg |
| Distilled water | Total | 1.0 ml |

The above components are mixed and the mixture is treated with an ultrasonic to prepare 1 ml ampoule.

What is claimed is:

1. A method for treating consciousness disorder and perception and movement disorder which comprises treating a person suffering from said disorders by administering a therapeutically effective amount of a phosphatidylcholine of the formula:

$$\begin{array}{l} CH_2-O-R_1 \\ | \\ R_2-O-CH \quad\quad O \quad\quad\quad CH_3 \\ | \quad\quad\quad\quad || \quad\quad\quad / \\ CH_2-O-P-O-CH_2CH_2N^+-CH_3 \\ | \quad\quad\quad\quad\quad\quad\quad \backslash \\ O^- \quad\quad\quad\quad\quad\quad CH_3 \end{array} \quad (I)$$

wherein $R_1$ and $R_2$ are the same or different and are each hydrogen, a residue of a saturated fatty acid having 6 to 22 carbon atoms, or residue of an unsaturated fatty acid having 14 to 20 carbon atoms, provided that at least one of $R_1$ and $R_2$ is a residue of the said saturated or unsaturated fatty acid.

2. A method according to claim 1, wherein the phosphatidylcholine is a compound of the formula [I] wherein at least one of $R_1$ and $R_2$ is a residue of an unsaturated fatty acid having 14 to 20 carbon atoms.

3. A method according to claim 1, wherein the phosphatidylcholine is a compound of the formula [I] wherein both of $R_1$ and $R_2$ are a residue of an unsaturated fatty acid having 14 to 20 carbon atoms.

4. A method according to claim 2, wherein the residue of an unsaturated fatty acid is a member selected from the group consisting of linoleoyl, linolenoyl and arachidonyl.

5. A method according to claim 3, wherein the residue of an unsaturated fatty acid is a member selected from the group consisting of linoleoyl, linolenoyl and arachidonyl.

6. A method according to claim 1, wherein the phosphatidylcholine is a member selected from the group consisting of soy bean phosphatidylcholine, yolk phosphatidylcholine, soy bean lysophosphatidylcholine, 1,2-dihexanoylphosphatidylcholine, 1-palmitoyl-2-linoleoylphosphatidylcholine, 1-linoleoyl-2-palmitoylphosphatidylcholine, 1,2-dilinoleoylphosphatidylcholine, and 1,2-diarachidonylphosphatidylcholine.

7. A method according to claim 6, wherein the phosphatidylcholine is a member selected from the group consisting of soy bean phosphatidylcholine, soy bean lysophosphatidylcholine, 1,2-dihexanoylphosphatidylcholine, and 1,2-dilinoleoylphosphatidylcholine.

8. A method according to claim 7, wherein the phosphatidylcholine is soy bean phosphatidylcholine.

9. A method according to claim 1, wherein the phosphatidylcholine is administered by a parenteral route in a dose of 1 to 1,500 mg per day.

10. A method according to claim 1, wherein the phosphatidylcholine is administered by oral route in a dose of 10 mg to 15 g per day.

11. A method for treating consciousness disorder and perception and movement disorder, which comprises parenterally administering the phosphatidylcholine of claim 9 to a patient suffering from the disease in a dose of 1 to 1,500 mg per day.

12. A method according to claim 11, wherein the agent is administered in an intravenous route.

* * * * *